United States Patent
Khosravi

[11] Patent Number: 6,129,739
[45] Date of Patent: Oct. 10, 2000

[54] VASCULAR DEVICE HAVING ONE OR MORE ARTICULATION REGIONS AND METHODS OF USE

[75] Inventor: Farhad Khosravi, San Mateo, Calif.

[73] Assignee: Incept LLC, San Mateo, Calif.

[21] Appl. No.: 09/470,857

[22] Filed: Dec. 23, 1999

Related U.S. Application Data

[63] Continuation of application No. 09/364,064, Jul. 30, 1999.

[51] Int. Cl.[7] .................................................. A61M 29/00
[52] U.S. Cl. ........................................... 606/200; 606/194
[58] Field of Search ................................... 606/200, 194, 606/198, 159; 604/96, 22

[56] References Cited

U.S. PATENT DOCUMENTS

| | | | |
|---|---|---|---|
| 3,592,186 | 7/1971 | Oster | 128/2 R |
| 3,683,904 | 8/1972 | Forster | 128/127 |
| 3,952,747 | 4/1976 | Kimmell, Jr. | 128/303 R |
| 3,996,938 | 12/1976 | Clark, III | 128/348 |
| 4,046,150 | 9/1977 | Schwartz et al. | 128/328 |
| 4,662,885 | 5/1987 | DiPisa, Jr. | 623/12 |
| 4,705,517 | 11/1987 | DiPisa, Jr. | 623/12 |
| 4,706,671 | 11/1987 | Weinrib | 128/348 |
| 4,723,549 | 2/1988 | Wholey et al. | 128/344 |
| 4,784,928 | 2/1989 | Kletschka | 128/344 |
| 4,790,812 | 12/1988 | Hawkins, Jr. et al. | 604/22 |
| 4,807,626 | 2/1989 | McGirr | 128/328 |
| 4,873,978 | 10/1989 | Ginsburg | 128/345 |
| 4,921,478 | 5/1990 | Solano et al. | 604/53 |
| 4,921,484 | 5/1990 | Hillstead | 604/104 |

(List continued on next page.)

FOREIGN PATENT DOCUMENTS

| | | | |
|---|---|---|---|
| 0 427 429 A1 | 5/1991 | European Pat. Off. | A61M 25/10 |
| 0 655 228 A1 | 11/1994 | European Pat. Off. | A61F 2/02 |
| 0 737 450 A1 | 10/1996 | European Pat. Off. | A61F 2/01 |
| 0 743 046 A1 | 11/1996 | European Pat. Off. | A61F 2/01 |
| 0 759 287 A1 | 2/1997 | European Pat. Off. | A61F 2/01 |
| 0 771 549 A2 | 5/1997 | European Pat. Off. | A61F 2/01 |
| 0 784 988 A1 | 7/1997 | European Pat. Off. | A61M 5/165 |
| 0 852 132 A1 | 7/1998 | European Pat. Off. | A61F 2/01 |
| 2 020 557 | 11/1979 | United Kingdom | A61B 17/50 |
| WO 94/14389 | 7/1994 | WIPO | A61F 2/02 |
| WO 96/01591 | 1/1996 | WIPO | A61B 17/22 |
| WO 97/27808 | 8/1997 | WIPO | A61B 17/22 |
| WO 97/42879 | 11/1997 | WIPO | A61B 17/00 |
| WO 98/23322 | 6/1998 | WIPO | A61M 29/00 |
| WO 98/33443 | 8/1998 | WIPO | A61B 17/22 |
| WO 98/34673 | 8/1998 | WIPO | A61M 31/00 |
| WO 98/36786 | 8/1998 | WIPO | A61M 5/32 |
| WO 98/38920 | 9/1998 | WIPO | A61B 17/22 |
| WO 98/38929 | 9/1998 | WIPO | A61B 17/00 |
| WO 98/39053 | 9/1998 | WIPO | A61M 29/00 |
| WO 98/46297 | 10/1998 | WIPO | A61M 29/00 |
| WO 98/47447 | 10/1998 | WIPO | A61F 2/06 |
| WO 98/50103 | 11/1998 | WIPO | A61M 29/00 |
| WO 98/51237 | 11/1998 | WIPO | A61F 2/01 |
| WO 98/55175 | 12/1998 | WIPO | A61M 29/00 |
| WO 99/09895 | 3/1999 | WIPO | A61B 17/12 |
| WO 99/23976 | 5/1999 | WIPO | A61F 2/01 |

OTHER PUBLICATIONS

Wholey, Mark H. et al., "PTA and Stents in the Treatment of Extracranial Circulation," *The Journal of Invasive Cardiology*: vol. 8/Supplement E, Health Management Publications, Inc., 1996, pp. 25E–30E.

*Primary Examiner*—Gary Jackson
*Attorney, Agent, or Firm*—Fish & Neave; Nicola A. Pisano; Kenneth J. Michlitsch

[57] ABSTRACT

Apparatus and methods are provided for use in filtering emboli from a vessel and performing thrombectomy and embolectomy, wherein a vascular device comprises one or more support hoops, each having an articulation region connected near a distal end of a guide wire, and a blood permeable sac affixed to the support hoop or hoops to form a mouth of the blood permeable sac. The mouth of the sac closes when the apparatus is collapsed for removal to prevent material from escaping from the sac.

23 Claims, 5 Drawing Sheets

U.S. PATENT DOCUMENTS

| | | | |
|---|---|---|---|
| 4,926,858 | 5/1990 | Gifford et al. | 606/159 |
| 4,969,891 | 11/1990 | Gewertz | 606/200 |
| 4,998,539 | 3/1991 | Delsanti | 128/898 |
| 5,002,560 | 3/1991 | Machold et al. | 606/198 |
| 5,011,488 | 4/1991 | Ginsburg | 606/159 |
| 5,053,008 | 10/1991 | Bajaj | 604/104 |
| 5,071,407 | 12/1991 | Termin et al. | 604/104 |
| 5,102,415 | 4/1992 | Guenther et al. | 606/159 |
| 5,108,419 | 4/1992 | Reger et al. | 606/200 |
| 5,133,733 | 7/1992 | Rasmussen et al. | 606/200 |
| 5,171,233 | 12/1992 | Amplatz et al. | 604/281 |
| 5,329,942 | 7/1994 | Gunther et al. | 128/898 |
| 5,354,310 | 10/1994 | Garnic et al. | 606/196 |
| 5,370,657 | 12/1994 | Irie | 606/200 |
| 5,383,887 | 1/1995 | Nadal | 606/200 |
| 5,415,630 | 5/1995 | Gory et al. | 604/53 |
| 5,421,832 | 6/1995 | Lefebvre | 604/53 |
| 5,456,667 | 10/1995 | Ham et al. | 604/107 |
| 5,476,104 | 12/1995 | Sheahon | 128/757 |
| 5,549,626 | 8/1996 | Miller et al. | 606/200 |
| 5,658,296 | 8/1997 | Bates et al. | 606/127 |
| 5,662,671 | 9/1997 | Barbut et al. | 606/170 |
| 5,669,933 | 9/1997 | Simon et al. | 600/200 |
| 5,695,519 | 12/1997 | Summers et al. | 606/200 |
| 5,746,758 | 5/1998 | Nordgren et al. | 606/159 |
| 5,769,816 | 6/1998 | Barbut et al. | 604/96 |
| 5,779,716 | 7/1998 | Cano et al. | 606/114 |
| 5,792,300 | 8/1998 | Inderbitzen et al. | 156/244.13 |
| 5,795,322 | 8/1998 | Boudewijn | 604/22 |
| 5,797,952 | 8/1998 | Klein | 606/198 |
| 5,800,457 | 9/1998 | Gelbfish | 606/200 |
| 5,800,525 | 9/1998 | Bachinski et al. | 623/1 |
| 5,814,064 | 9/1998 | Daniel et al. | 606/200 |
| 5,817,102 | 10/1998 | Johnson et al. | 60/108 |
| 5,827,324 | 10/1998 | Cassell et al. | 606/200 |
| 5,833,644 | 11/1998 | Zadno-Azizi et al. | 604/52 |
| 5,833,650 | 11/1998 | Imran | 604/53 |
| 5,846,260 | 12/1998 | Maahs | 606/200 |
| 5,876,367 | 3/1999 | Kaganov et al. | 604/8 |
| 5,893,867 | 4/1999 | Bagaoisan et al. | 606/198 |
| 5,895,399 | 4/1999 | Barbut et al. | 606/159 |
| 5,954,745 | 9/1999 | Gertler et al. | 606/200 |

VASCULAR DEVICE HAVING ONE OR MORE ARTICULATION REGIONS AND METHODS OF USE

REFERENCE TO RELATED APPLICATION

The present application is a continuation-in-part application of copending U.S. patent application Ser. No. 09/364,064 filed Jul. 30, 1999.

FIELD OF THE INVENTION

The present invention relates to apparatus and methods for filtering or removing matter from within a vascular system. More particularly, the present invention provides a low profile self-expanding vascular device useful for capturing emboli generated during interventional procedures, and for thrombectomy and embolectomy.

BACKGROUND OF THE INVENTION

Percutaneous interventional procedures to treat occlusive vascular disease, such as angioplasty, atherectomy and stenting, often dislodge material from the vessel walls. This dislodged material, known as emboli, enters the bloodstream, and may be large enough to occlude smaller downstream vessels, potentially blocking blood flow to tissue. The resulting ischemia poses a serious threat to the health or life of a patient if the blockage occurs in critical tissue, such as the heart, lungs, or brain.

The deployment of stents and stent-grafts to treat vascular disease, such as aneurysms, also involves the introduction of foreign objects into the bloodstream, and also may result in the formation of clots or release of emboli. Such particulate matter, if released into the bloodstream, also may cause infarction or stroke.

Numerous previously known methods and apparatus have been proposed to reduce the risk of embolism. U.S. Pat. No. 5,833,644 to Zadno-Azizi et al., for example, describes the use of a balloon-tipped catheter to temporarily occlude flow through a vessel from which a stenosis is to be removed. Stenotic material removed during a treatment procedure is evacuated from the vessel before the flow of blood is restored. A drawback of such previously known systems, however, is that occlusion of antegrade flow through the vessel may result in damage to the tissue normally fed by the blocked vessel.

U.S. Pat. No. 5,814,064 to Daniel et al. describes an emboli filter system having a radially expandable mesh filter disposed on the distal end of a guide wire. The filter is deployed distal to a region of stenosis, and any interventional devices, such as angioplasty balloons or stent delivery systems, are advanced along the guide wire. The filter is designed to capture emboli generated during treatment of the stenosis while permitting blood to flow through the filter. Similar filter systems are described in U.S. Pat. No. 4,723,549 to Wholey et al. and U.S. Pat. No. 5,827,324 to Cassell et al.

One disadvantage of radially expandable filter systems such as described in the foregoing patents is the relative complexity of the devices, which typically comprise numerous parts. Connecting more than a minimal number of such parts to a guide wire generally reduces the ability of the guide wire to negotiate tortuous anatomy, and increases the profile of the device in its delivery configuration. Consequently, it may be difficult or impossible to use such devices in small diameter vessels such as are commonly found in the carotid artery and cerebral vasculature. Moreover, such filter devices are generally incapable of preventing material from escaping from the filter during the process of collapsing the filter for removal.

International Publication No. WO 98/39053 describes a filter system comprising an elongated member, a radially expandable hoop and a cone-shaped basket. The hoop is affixed to the elongated member, and the cone-shaped basket is attached to the hoop and the elongated member so that the hoop forms the mouth of the basket. The filter system includes a specially configured delivery catheter that retains the mouth of the basket in a radially retracted position during delivery.

While the filter system described in the foregoing International Publication reduces the number of components used to deploy the cone-shaped basket, compared to the radial strut-type filter elements described hereinabove, it too has drawbacks. Chief among these, it is expected that it will be difficult to reduce the diameter of the radially expandable hoop to its retracted position. In particular, as the hoop is contracted through smaller radii of curvature, the stiffness of the hoop is expected to increase dramatically. This increased stiffness prevents the hoop from being contracted more tightly, and is expected to result in a delivery profile too large to permit use of the device in critical regions of the body, such as the smaller coronary arteries, carotid arteries, and cerebral vasculature.

In view of the foregoing disadvantages of previously known apparatus and methods, it would be desirable to provide a vascular device, e.g., for use as a vascular filter that, overcomes such disadvantages, and employs few components.

It also would be desirable to provide a vascular device that is capable of being contracted to a small delivery profile, thus permitting use of the device in small vessels.

It further would be desirable to provide a vascular device that is capable of being contracted to a sufficiently small profile that it may be retrieved using the guide wire lumen of previously known treatment devices, and without the need for specialized delivery catheters.

It still further would be desirable to provide a vascular device that reduces the risk of emboli or thrombus removed from the vessel wall escaping from the device when the device is collapsed and removed.

SUMMARY OF THE INVENTION

In view of the foregoing, it is an object of the present invention to provide a vascular device that overcomes disadvantages of previously known vascular filters and thrombectomy/embolectomy devices, and employs few components.

It also is an object of this invention to provide a vascular device that is capable of being contracted to a small delivery profile, thus permitting use of the device in small vessels.

It is a further object of the present invention to provide a vascular device that is capable of being contracted to a sufficiently small profile that it may be retrieved using the guide wire lumen of previously known treatment devices, and without the need for specialized delivery catheters.

It is another object of this invention to provide a vascular device that reduces the risk of emboli or thrombus removed from the vessel wall escaping from the device when the device is collapsed and removed.

These and other objects of the present invention are accomplished by providing a vascular device, suitable for use as a vascular filter or thrombectomy/embolectomy device that comprises a blood permeable sac affixed at its perimeter to a support hoop having an articulation region. The support hoop is attached to a distal region of an elongated member, such as a guide wire, and supports a proximally-oriented mouth of the sac when the device is deployed in a vessel.

In accordance with the principles of the present invention, the support hoop includes a reduced-thickness articulation region that enables the support hoop to be contracted to very small radii of curvature without the problems of increased stiffness and kinking of previously known devices. Alternatively, the articulation region may comprise a gap in the support hoop bridged by the perimeter of the blood permeable sac.

The support hoop preferably also has a curved profile that prevents the articulation region, when folded, from damaging the wall of the vessel. The curved profile also permits the device to effectively contact the walls of the vessel and reduce emboli or thrombus removed from the vessel wall from bypassing the sac. Moreover, the articulation region when combined with a support hoop having a curved profile, causes the sides of the support hoop to fold inwards towards one-another when the vascular device is collapsed into a sheath for removal. This in turn closes the mouth of the sac and reduces the potential for emboli or thrombus to be released from the vascular device during removal.

Advantageously, use of an articulation region permits the vascular device of the present invention to be contracted to very small diameters, thereby enabling the use of delivery catheters having diameters as small as 3 Fr. Moreover, the vascular device of the present invention may be retracted within the guide wire lumen of conventional treatment devices, such as angioplasty catheters and stent delivery systems, thereby obviating the need to re-insert a specialized delivery catheter to remove the vascular device.

In embodiments of the system of the present invention suitable for use as embolic filters, the vascular device may include a separate guide wire for introducing treatment devices proximal of the deployed vascular device. Additionally, the vascular device may have a second support hoop attached to the distal end of the sac. During retrieval, multiple hoops ensure that emboli are retained within the sac and prevent the sac from bunching. Where two hoops are rotated, they also may be arranged to rotate independently of the guide wire, thereby reducing the risk that the sac wall become twisted during advancement.

In alternative embodiments, sac bunching is mitigated by tapering the sac and attaching it to one or more support hoops. Sac porosity may also be controlled to ensure passage of blood cells while capturing emboli and to control the pressure drop across the device. In yet other embodiments, a delivery sheath is provided that permits a lesion to first be crossed with an unencumbered guide wire prior to passing the vascular device across the lesion.

Methods of using the vascular device of the present invention are provided, including the use of novel radiopaque features.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1A:
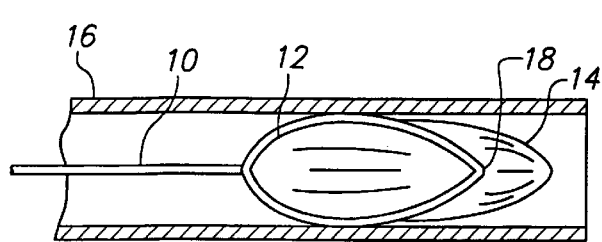
FIGS. 1A and 1B are, respectively, a side sectional view of a previously known vascular device contracted within a delivery sheath and an end view of that vascular device deployed in a vessel.
Figure 1B:
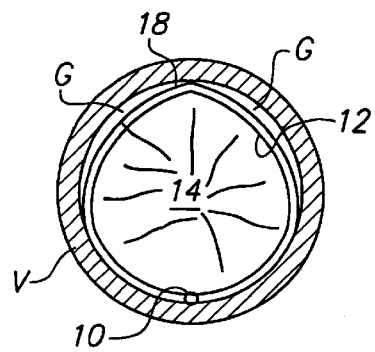

Referring to FIGS. 1A and 1B, some of the disadvantages associated with previously known vascular devices, such as the emboli filters described in the above-mentioned International Publication WO 98/39053, are described. Vascular filter comprises guide wire 10 having hoop 12 coupled to its end. Filter sac 14 is affixed to hoop 12, so that when delivery catheter 16 is retracted proximally and guide wire 10 is held stationary, hoop 12 radially expands to contact the walls of a vessel.

As described hereinabove, one difficulty with such vascular filters is that the hoop used to support the filter sac experiences increased stiffness when contracted to small diameters, i.e., due to the sharp directional change at the tip of the hoop, thereby limiting the minimum delivery profile achievable for such instruments. Although this effect may be reduced by decreasing the thickness of the wire employed in hoop 12, at the point at which the wire becomes sufficiently thin to accommodate the bending stresses, the wire is too thin to effectively radially expand and urge the filter sac into engagement with the vessel wall.

On the other hand, as shown in FIGS. 1A and 1B, the bending stresses imposed upon the hoop of such previously known devices, if drawn within a delivery catheter, may be sufficiently high to result in the formation of kink 18 at the tip of the hoop. This "kinking" effect becomes more severe in sheaths having a small inner diameter. Thus, for example, applicant has observed that when sheaths having inner diameters of 0.035" or smaller are used, a hoop of nitinol or multi-strand nitinol cable having a diameter of 0.0055" will form kink 18. Kink 18 in turn may apply relatively high localized pressure and friction against wall 17 of sheath 16, thereby making the vascular filter difficult to deploy. In particular, the kink may impale wall 17 of delivery sheath 16 and may make it difficult or impossible to deploy the vascular filter, especially in tortuous anatomy.

In addition, when the filter is subsequently deployed in vessel V, as shown in FIG. 1B, kink 18 may deform the pre-formed shape of hoop 12, impairing the ability of the filter to seal against the walls of vessel V. This may in turn lead to the presence of gaps G between the perimeter of the hoop and the vessel wall, depending upon the severity of the kink. Consequently, emboli may pass through the gaps with antegrade flow and significantly reduce the efficacy of the filter. Additionally, kink 18 may be sufficiently sharp to damage or dissect the wall of vessel V when the filter is deployed.

The vascular device of the present invention solves the above-described disadvantages, providing a vascular device, suitable for use as a vascular filter or thrombectomy/embolectomy device, with a self-expanding support hoop that is sufficiently thick to radially expand and urge a blood permeable sac into engagement with the vessel wall, but which includes an articulation region that overcomes the problems associated with kinking. In particular, the vascular device of the present invention includes a reduced thickness articulation region and a pre-formed curved profile that avoids the difficulties of previously known systems while providing a high degree of efficacy in capturing emboli or thrombus, and ease of deployment and retrieval.

Figure 2A:
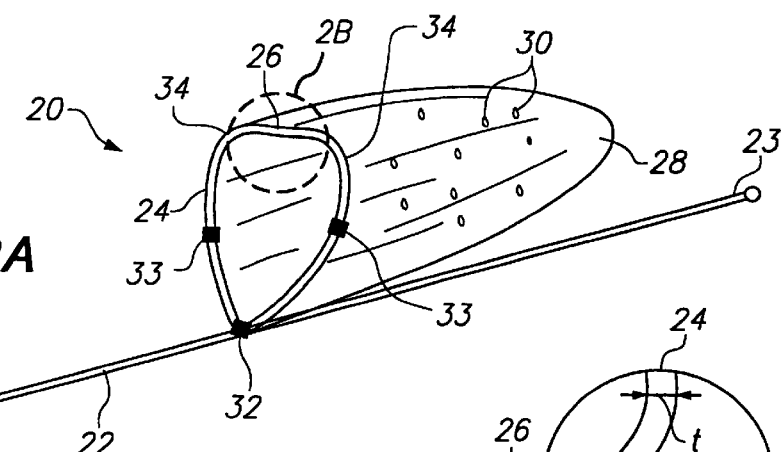
FIGS. 2A and 2B are, respectively, a perspective view of a vascular device constructed in accordance with the principles of the present invention in a deployed state, and a detailed view of the articulation region of the device of FIG. 2A.
Figure 2B:
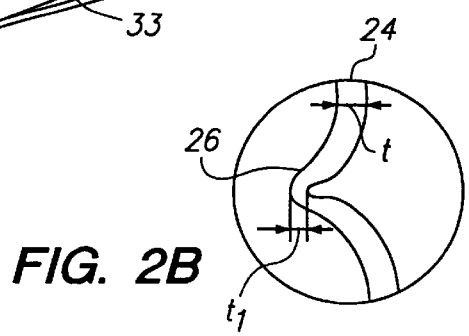

Referring now to FIGS. 2A and 2B, vascular device 20 constructed in accordance with the principles of the present invention, illustratively an embolic filter, comprises guide wire 22, support hoop 24 having articulation region 26, and blood permeable sac 28 affixed to support hoop 24. Sac 28 is coupled to support hoop 24 so that the support hoop 24 forms an opening for the sac. Support hoop 24 preferably is connected to guide wire 22 near distal end 23 of the guide wire.

Sac 28 preferably is constructed of a thin, flexible biocompatible material, such as polyethylene, polypropylene, polyurethane, polyester, polyethylene tetraphlalate, nylon or polytetrafluoroethylene, or combinations thereof, and includes openings or pores 30 that permit blood cells to pass through the sac substantially unhindered, while capturing any larger emboli that may be released during a procedure such as angioplasty or stent placement. In a preferred embodiment, sac 28 has openings or pores 30 in a range of about 20 to 400 microns in diameter, and more preferably, about approximately 80 microns. These pore sizes will permit red blood cells (which have a diameter of approximately 5 microns) to easily pass through the sac. If sac 28 comprises a woven material, such as formed from the above-mentioned polymers, the pore size of the sac may be determined as a function of the pattern and tightness of the weave.

Support hoop 24 comprises a hoop having a circular or rectangular cross-section that is formed of a super-elastic material, such as a nickel-titanium alloy ("nitinol"). During deployment and retrieval of vascular device 20, described hereinafter, support hoop 24 folds in half and collapses to fit within a small diameter delivery sheath. When vascular device 20 is in a deployed state, as depicted in FIG. 2A, support hoop 24 resumes its pre-formed shape. Support hoop 24 preferably comprises nitinol wire, although it may also be formed from a multi-strand nitinol cable, or other super-elastic material.

In accordance with the principles of the present invention, support hoop 24 includes one or more reduced-thickness articulation regions 26, and pre-formed curved regions 34. As depicted in FIG. 2B, articulation region 26 includes a region having reduced thickness $t_1$ compared to thickness t of the remainder of support hoop 24. Articulation region 26 and curved regions 34 enable support hoop 24 to fold with a pre-determined shape when vascular device 20 is collapsed to a contracted state for delivery or retrieval.

In FIG. 2B, articulation region 26 is depicted as a localized reduction in the thickness of support hoop 24, as may be achieved using conventional grinding or etching processes. Alternatively, support hoop 24 may be continuously tapered along its circumference, so that articulation region results from a more gradual reduction in the wall thickness of the support hoop. Tapering support hoop 24 may permit greater flexibility in the vicinity of articulation region 26, thus enabling support hoop 24 to fold more easily at the articulation region. Such tapering of the thickness of the support hoop along a portion of its circumference also may reduce the potential for stress-induced fracture typically associated with abrupt changes in diameter.

In a preferred embodiment of the vascular device 20 of the present invention, vascular device 20 easily fits within a delivery sheath having an inner diameter of 0.033", and more preferably, may be used with a delivery sheath having an inner diameter as small as 0.026". The deployed diameter of support hoop 24 preferably is approximately 7 mm, while guide wire 22 preferably has a diameter of 0.014", and tapers at its distal end. The distal end of guide wire 22 also may be tipped with a spring section, or coil tip (not shown).

Support hoop 24 preferably is constructed of 0.0055" nitinol wire tapered (by a grinding process) to 0.0025" at articulation region 26. Specifically, articulation region 26 preferably consists of a length about 0.05" long and having a diameter of 0.0025", coupled on either side to curved regions 34. Each of curved regions 34 includes of a length of wire that is tapered from a diameter of 0.055" to a diameter of 0.0025" over a length of about 0.025". Support hoop 24 also may include radiopaque features, such as gold or platinum bands 33, spaced at intervals around the circumference of support hoop 24, or a coil of radiopaque material wrapped around the support hoop, as described hereinafter with respect to FIG. 10.

Figure 3:
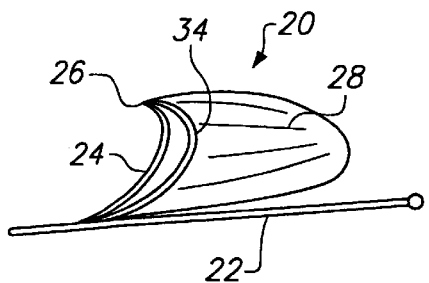
FIG. 3 is a perspective view of the vascular device of the present invention in a folded configuration, prior to removal.
Figure 4:
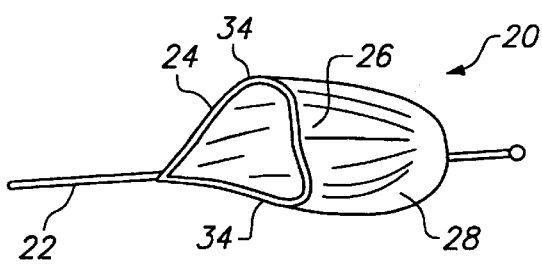
FIG. 4 is a plan view of the vascular device of FIG. 2A.

Referring to FIGS. 3 and 4, additional features of vascular device 20 are described. FIG. 3 depicts vascular device 20 of FIG. 2A in a contracted state, while FIG. 4 illustrates a directional change in support hoop 24 preferably caused by the presence of curved regions 34. In the embodiment depicted in FIG. 4, curved regions 34 illustratively are configured to orient articulation region 26 in a direction parallel to the axis of guide wire 22.

Advantageously, use of articulation region 26 and the curved profile of support hoop 24 introduced by curved regions 34 also cause support hoop 24 to fold in half during retrieval. As shown in FIG. 3, support hoop 24 folds in half, effectively closing the mouth of blood permeable sac 28 and preventing the escape of collected emboli or thrombus. This feature also may permit the use of a smaller or shallower sac than would otherwise be possible, without increasing the risk of material escaping from the device when the sac is collapsed for retrieval. Use of a smaller or shallower sac also enables vascular device 20 to be delivered in a smaller delivery sheath, having an inner diameter as small as 0.026" for the preferred embodiment.

Figure 5A:
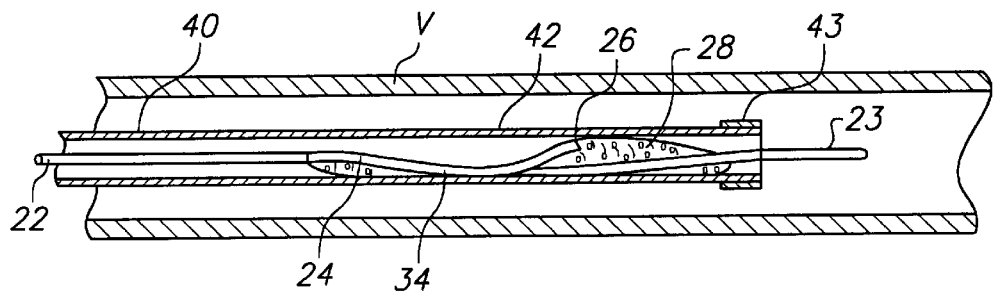
FIGS. 5A–5D are side sectional views depicting a method of deploying, using, and retrieving the vascular device of the present invention.

Referring now to FIGS. 5A–5D, methods of using the vascular device of the present invention as a vascular filter are described. In FIG. 5A, guide wire 22 is manipulated into position within vessel V using well-known percutaneous techniques. Vascular device 20 of FIG. 2A is disposed in its contracted delivery state within distal end 42 of delivery sheath 40 and delivery sheath 40 is advanced through the vessel using distal end 23 of guide wire 22. Articulation region 26 and curved regions 34 of support hoop 24 enable the sides of the support hoop to fold together and become elongated when drawn within delivery sheath 40.

Figure 5B:
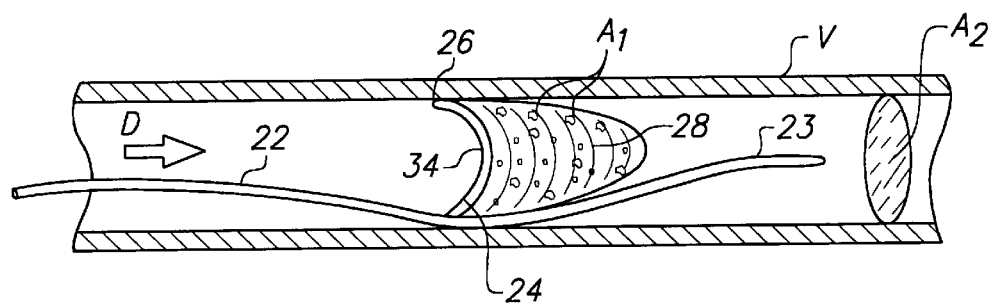

With respect to FIG. 5B, once delivery sheath 40 is disposed at a desired location within a patient's vessel V, such as a coronary artery or carotid artery, for example, based on the position of radiopaque band 43 under a fluoroscope, guide wire 22 is held stationary while delivery sheath 40 is retracted proximally. Alternatively, delivery sheath 40 may be held stationary while guide wire 22 is advanced. In either case, when vascular device 20 is no longer confined within delivery sheath 40, support hoop 24 expands to seal against the walls of the vessel V. When in its deployed state, curved regions 34 of support hoop 24 orient articulation region 26 along the axis of the vessel, thus reducing the risk of impaling the vessel wall, as might be expected of the kinked support hoop of FIG. 1B. Blood continues to flow unimpeded through vessel V in direction D.

Figure 5C:
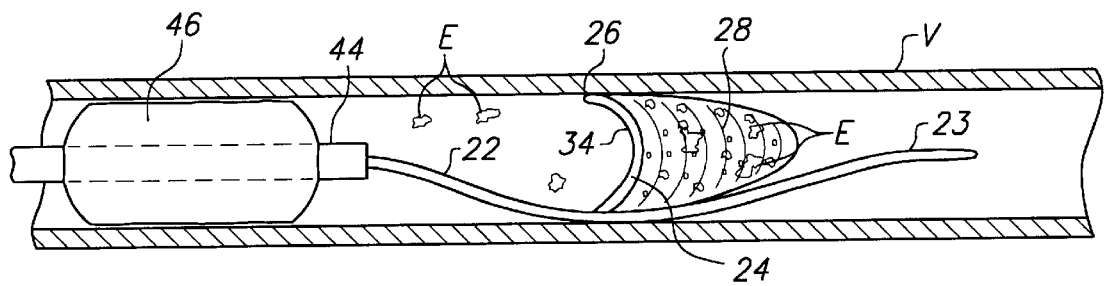

In FIG. 5C, once vascular device 20 is deployed in vessel V, other interventional instruments, such as angioplasty catheters, atherectomy devices, or stent delivery systems may be advanced along guide wire 22 to position such devices at treatment zones located proximally of vascular device 20. For example, in FIG. 5C, angioplasty balloon catheter 44 has been advanced along guide wire 22 to a position proximal of vascular device 20 to trap emboli E, i.e., pieces of plaque dislodged from the walls of vessel V by balloon 46.

Figure 5D:
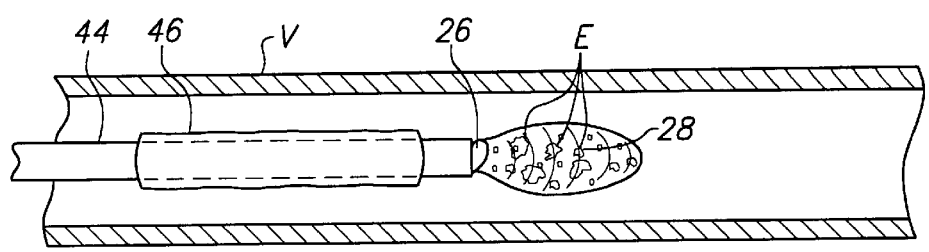

With respect to FIG. 5D, upon completion of the angioplasty procedure using angioplasty balloon catheter 44, guide wire 22 is pulled proximally to cause the sides of support hoop 24 to collapse together to close the mouth of sac 28 (see FIG. 3). Additional proximal retraction of guide wire 22 causes support hoop 24 and sac 28 to enter at least partially within the guide wire lumen of angioplasty catheter 44. As depicted in FIG. 5D, only a portion of support hoop 24, near articulation region 26, and a distal portion of sac 28 extend out of the guide wire lumen of angioplasty catheter 44. Angioplasty catheter 44 then is withdrawn with vascular device 20 and any trapped emboli E.

Advantageously, the compliant design of vascular device 20 permits the device to be contracted to its delivery state within the guide wire lumen of conventional previously known interventional devices. ccordingly, unlike previously known vascular devices, which require removal of the interventional device followed by re-insertion of a specially designed catheter to retrieve the vascular device, the system of the present invention reduces the time, effort and trauma of this additional step. Instead, the vascular device may be readily closed and retrieved upon completion of the interventional procedure.

Alternatively, vascular device 20 may be used in performing thrombectomy/embolectomy. In this case, the vascular device is deployed in a vessel at a location distal to a lesion, in the manner depicted in FIGS. 5A and 5B. Once support hoop 24 is deployed into contact with the vessel wall, vascular device 20 may be retracted proximally to scrape along the wall of the vessel, and excise thrombus so that it is captured in sac 28. Delivery sheath 44 may then be re-inserted into the vessel along guide wire 22, and vascular device 20 is retracted and removed from the vessel.

As discussed hereinabove, sac 28 is porous so that blood cells may pass through while emboli E are captured. As seen in FIG. 5B, if the sum of the area of all these pores $A_1$ is less than the internal cross-sectional area $A_2$ of vessel V, a pressure drop is expected across the vascular device. This may lead to hemolysis and insufficient downstream flow. If $A_1$ is greater than or equal to $A_2$, the pressure drop approaches zero. Proper selection of pore diameter (in the range of 20–400 microns) and pore density ensures that $A_1$ is greater than or equal to $A_2$.

Figure 6:
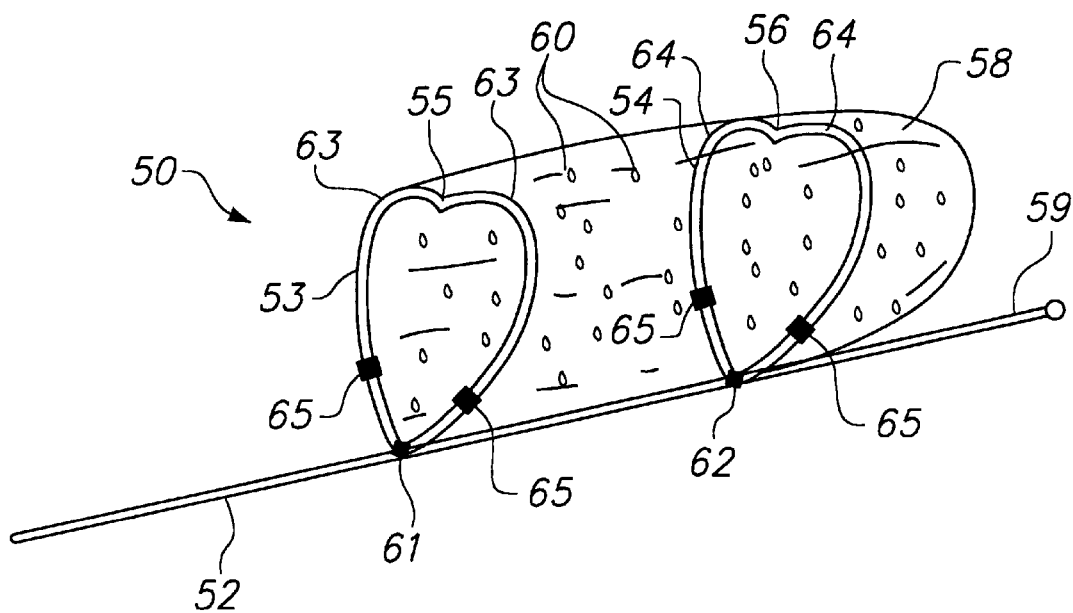
FIG. 6 is a perspective view of an alternative embodiment of the vascular device of the present invention with two support hoops, shown in a deployed state.

Referring now to FIGS. 6–9, further alternative embodiments of the vascular device of the present invention are described. In FIG. 6, vascular device 50, illustratively an embolic filter, comprises guide wire 52, support hoops 53 and 54 having articulation regions 55 and 56, respectively, and blood permeable sac 58 affixed to support hoops 53 and 54. Sac 58 is coupled to support hoop 53 at its proximal end so that the support hoop forms an opening for the sac. Sac 58 is coupled to support hoop 54 at its distal end to prevent emboli from spilling from sac 58 during retrieval. Support hoops 53 and 54 preferably are connected to guide wire 52 near distal end 59 of the guide wire. Sac 58 has openings or pores 60 that permit red blood cells to easily pass through the sac.

During deployment and retrieval of vascular device 50, support hoops 53 and 54 expand and collapse as discussed hereinabove with respect to support hoop 24 of FIGS. 2. Support hoops 53 and 54 are attached to guide wire 52 at attachment points 61 and 62, respectively, and further comprise curved regions 63 and 64, respectively. Support hoops 53 and 54 may include radiopaque features, such as gold or platinum bands 65, spaced at intervals around the circumference of the hoops.

Applicant expects that vascular device 50 may further reduce the risk that captured emboli could spill during retrieval, and also may provide a better seal against the artery.

Figure 7:
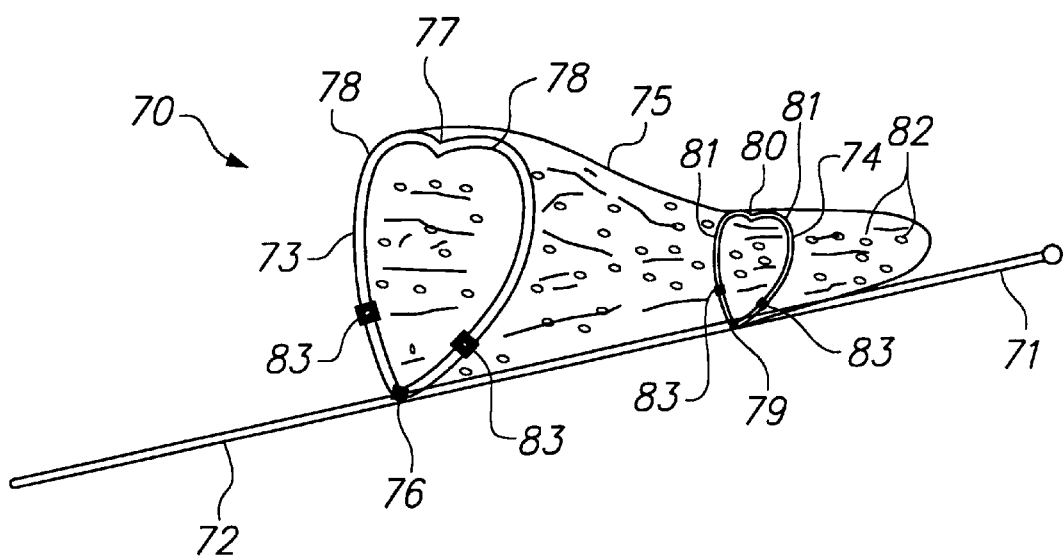
FIG. 7 is a perspective view of an alternative embodiment of the vascular device of FIG. 6 with a smaller distal support hoop.

With reference to FIG. 7, an alternative embodiment of vascular device 50 that prevents bunching is disclosed that may provide even further benefits. Vascular device 70 comprises guide wire 72 on which proximal support hoop 73 and distal support hoop 74 are disposed. The proximal and distal portions of blood permeable sac 75 are affixed to support hoops 73 and 74, respectively. Proximal support hoop 73 is attached to distal end 71 of guide wire 72 at attachment point 76 and includes articulation region 77 and curved regions 78. Likewise, distal support hoop 74 is attached to guide wire 72 at attachment point 79 and includes articulation region 80 and curved regions 81. Sac 75 includes blood permeable pores 82. Hoops 73 and 74 may include radiopaque features, such as gold or platinum bands 83, spaced at intervals around the circumference of the hoops.

Proximal support hoop 73 is significantly larger in circumference than distal hoop 74. Proximal hoop 73 seals against the artery walls and defines the diameter of the mouth of sac 75. Smaller distal hoop 74 prevents emboli from spilling from sac 75 when retrieving device 70. It also allows the diameter of sac 75 to decrease along its length. This taper in sac 75 is expected to reduce the risk that sac 75 will bunch when the sac is retrieved.

Applicant has determined that where multiple support hoops are employed, as in the embodiments of FIGS. 6 and 7, twisting of the guide wire during deployment may prevent the sac of the vascular device from properly sealing against the vessel wall. For example, if guide wire 52 in the embodiment of FIG. 6 is rotated after distal hoop 54 has been deployed, but before proximal hoop 53 has been deployed, proximal hoop 53 may deploy at an angle with respect to distal hoop 54. This, in turn, may constrict or all together close the opening of sac 58, thereby rendering the vascular device ineffective.

Figure 8:
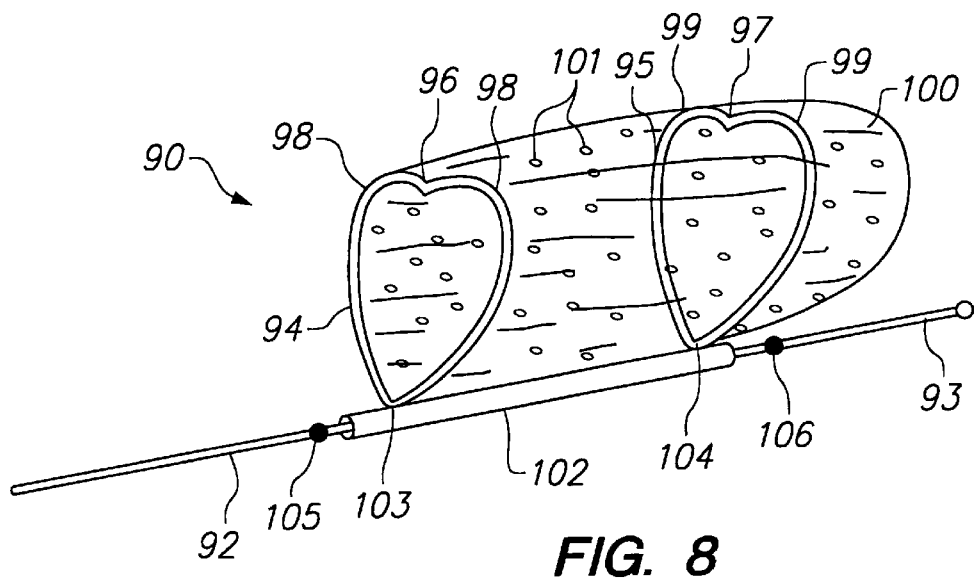
FIG. 8 is a perspective view of a still further alternative embodiment of the vascular device of FIG. 6 that allows the vascular device to independently rotate with respect to the guide wire.

FIG. 8 discloses a vascular device in accordance with the present invention that overcomes problems associated with twisting of the guide wire during deployment. Vascular device 90 comprises guide wire 92 with distal end 93, and support hoops 94 and 95. Support hoops 94 and 95 further comprise articulation regions 96 and 97, respectively, and curved regions 98 and 99, respectively. The proximal and distal portions of blood permeable sac 100 are attached to support hoops 94 and 95, respectively. Sac 100 includes pores 101. Support hoops 94 and 95 are attached to sheath 102 at attachment points 103 and 104, respectively. Sheath 102 preferably comprises a flexible, 0.001" thick tube made of a biocompatible material, such as polyamide or polytetraethylene. Guide wire 92 passes through the lumen of sheath 102. Sheath 102 is able to rotate with respect to guide wire 92 but is translationally restrained by stops 105 and 106, for example, solder beads.

By attaching support hoops 94 and 95 to sheath 102, rotational problems are mitigated. Sheath 102 only transmits translational motion of guide wire 92 to support hoops 94 and 95. Thus, twisting moments applied to wire 92 will not affect the performance of vascular device 90.

Figure 9:
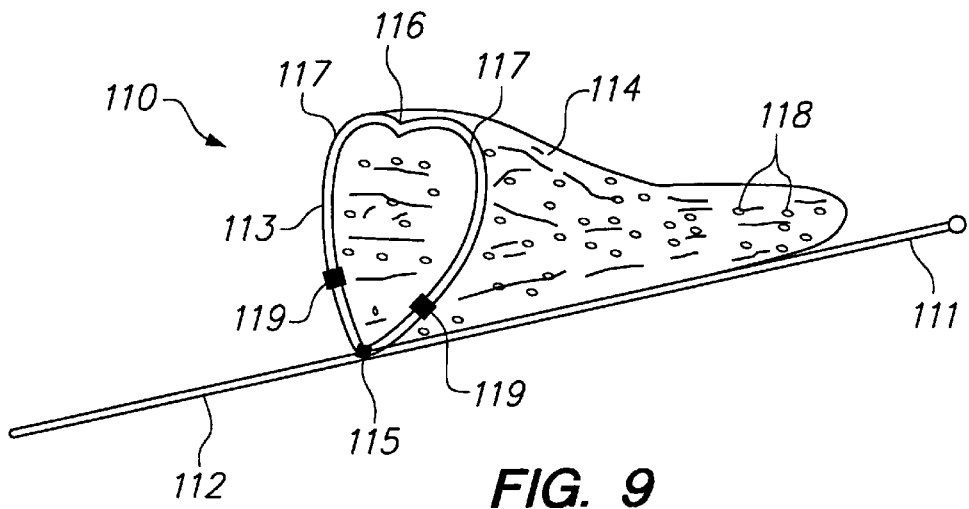
FIG. 9 is a perspective view of an alternative embodiment of the vascular device with a tapered blood permeable sac constructed in accordance with the principles of the present invention in a deployed state.

With reference to FIG. 9, a further alternative embodiment of the vascular device of the present invention is disclosed that also prevents bunching. Vascular device 110 comprises guide wire 112 on which support hoop 113 is disposed. Tapered blood permeable sac 114 is affixed to support hoop 113. Hoop 113 is attached to distal end 111 of guide wire 112 at attachment point 115 and includes articulation region 116 and curved regions 117. Tapered sac 114 includes blood permeable pores 118. Hoop 113 may include radiopaque features, such as gold or platinum bands 119, spaced at intervals around the circumference of the hoop.

As with vascular device 70 of FIG. 7, the diameter of tapered sac 114 decreases along its length to reduce the risk of bunching when the sac is retrieved. However, because vascular device 110 lacks the distal support hoop of the embodiments of FIGS. 6 and 7, there is a reduced risk of problems associated with twisting. In a preferred embodiment, the diameter at the distal end of tapered sac 114 is less than the internal diameter of the retrieval sheath with which the apparatus is used.

Figure 10:
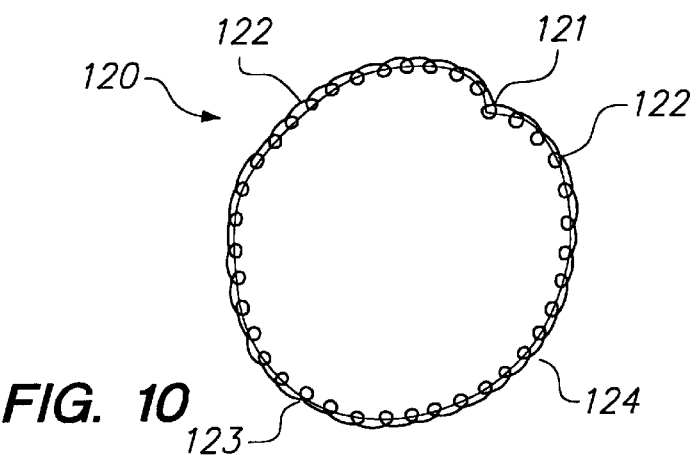
FIG. 10 is a perspective view of a radiopaque support hoop constructed in accordance with one aspect of the present invention.

Referring now to FIG. 10, a support hoop including a radiopaque feature is disclosed. Support hoop 120, illustratively shown in the deployed state, comprises articulation region 121, curved regions 122, attachment point 123, and wound radiopaque wire 124. In the preferred embodiment, wire 124 is platinum and is either round or a strip approximately 0.001" in diameter. Wire 124 is wrapped around hoop 120 all along its circumference.

One method of making a vascular device radiopaque is to electroplate platinum or gold onto the device. However, where the hoop is constructed of a nitinol material, electroplating can cause the nitinol wire to harden and become brittle. Because the hoop must change shape during deployment and retrieval, increased hardness and brittleness are undesirable characteristics and may promote failure of the support hoop. By wrapping wire 124, hoop 120 maintains its strength and flexibility. Radiopaque wire 124 may be used in conjunction with any of the vascular devices discussed herein.

Figure 11A:
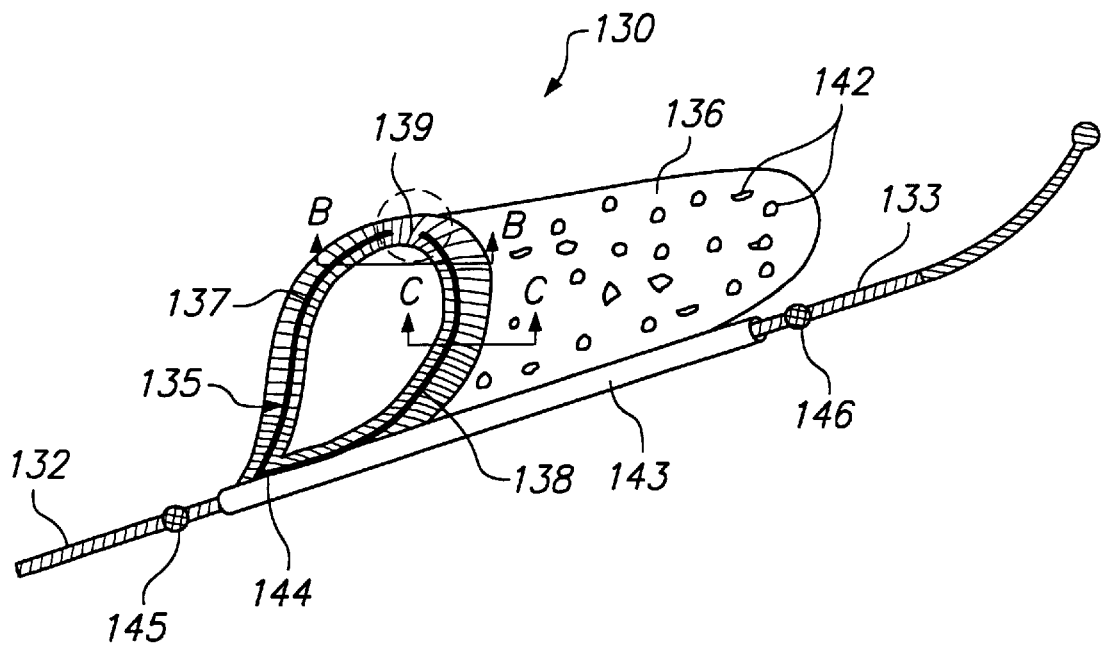
FIGS. 11A–11C illustrate another alternative embodiment of the vascular device of the present invention in which the articulation region comprises a gap in the support hoop bridged by the perimeter of the blood permeable sac.
Figure 11B:
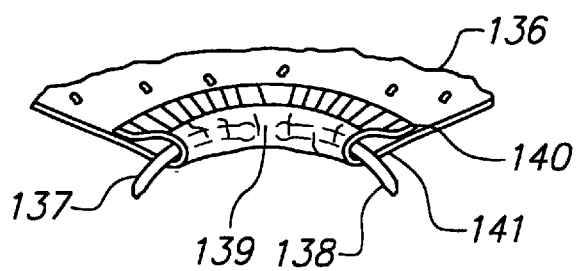
Figure 11C:
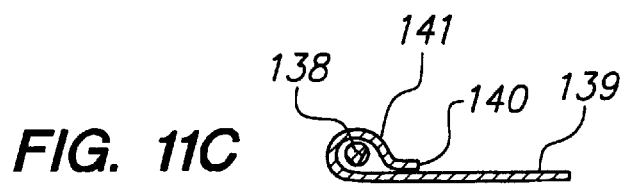

Referring now to FIGS. 11A–11C, another alternative embodiment of the vascular device of the present invention is described. As illustrated in FIG. 11A, vascular device 130 comprises guide wire 132 with distal region 133, wishbone support hoop 135, and blood permeable sac 136. Wishbone hoop 135 comprises spines 137 and 138 separated by a gap that serves as articulation region 139. Articulation region 139 is shown in greater detail in FIG. 11B, which corresponds to the area circled in FIG. 11A taken along section line B—B. Blood permeable sac 136 is wrapped around and attached to itself all along its perimeter, creating hem bond 140 and lumen 141. Sac 136 includes pores 147. Lumen 141 is configured to receive spines 137 and 138 and bridge the gap between them. FIG. 11C is a sectional view taken along line C—C of FIG. 11A, showing hem bond 140 and lumen 141 with spine 138 passing there through.

Referring again to FIG. 11A, wishbone support hoop 135 is attached to sheath 143 at attachment point 144. Sheath 143 is similar to sheath 102 of the embodiment of FIG. 8, and preferably comprises a flexible, 0.001" thick tube made of a biocompatible material, such as polyamide or polytetraethylene. Distal end 133 of guide wire 132 passes through the lumen of sheath 143. Sheath 143 may rotate with respect to guide wire 132 but is translationally restrained by stops 145 and 146, for example, solder beads. Sheath 143 mitigates rotational problems by only transmitting translational motion of guide wire 132 to wishbone hoop 135. Twisting moments applied to wire 132 do not affect the performance of vascular device 130.

The wishbone design of support hoop 135 advantageously enables a wider variety of materials to be used to fabricate the support hoop. Articulation region 139 allows vascular device 130 to deploy and contract in a manner similar to that described above for alternative embodiments. Deployment and retraction of wishbone hoop 135 induces minimal deformation of spines 137 and 138, thereby permitting use of materials such as spring steel. As will of course be apparent, the support hoop of the embodiment of FIGS. 11A–11C may advantageously be incorporated in any of the foregoing embodiments.

The support hoops depicted illustratively are shown as oval or heart-shaped in the deployed state, where the shape is exaggerated for the sake of clarity. In preferred embodiments, the support hoops are substantially round when deployed, to ensure contact around the circumference of the support hoop and provide a positive seal against the arterial wall.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. Apparatus for filtering emboli or performing thrombectomy or embolectomy, the apparatus comprising:

an elongated member having a distal region;

a support hoop coupled to the distal region having an articulation region comprising a gap interposed between curved spines; and a blood permeable sac affixed at its proximal end to the support hoop so that the gap is bridged by a portion of the blood permeable sac, and the hoop forms a mouth of the blood permeable sac.

2. The apparatus of claim 1, wherein the proximal end of the blood permeable sac comprises a lumen.

3. The apparatus of claim 2, wherein the lumen is configured to receive the curved spines and bridge the gap.

4. The apparatus of claim 1, wherein the blood permeable sac comprises a biocompatible material.

5. The apparatus of claim 4, wherein the biocompatible material comprises a material chosen from a list consisting of polyethylene, polypropylene, polyester, polyurethane and nylon.

6. The apparatus of claim 1, wherein the blood permeable sac comprises a plurality of pores, each one of the plurality of pores having a diameter in a range of 20 to 400 microns.

7. The apparatus of claim 6, wherein each one of the plurality of pores has a cross-sectional area, and a sum area of the cross-sectional areas is greater than or equal to a cross-sectional area of a patient's vessel.

8. The apparatus of claim 1, wherein the spines of the support hoop comprise an elastic material.

9. The apparatus of claim 1, wherein the apparatus has a deployed state, wherein the support hoop engages an interior wall of a patient's vessel, and a delivery state, wherein the apparatus has a contracted configuration to permit insertion within a delivery sheath.

10. The apparatus of claim 9, wherein the support hoop is folded at its articulation region when the apparatus is in the delivery state.

11. The apparatus of claim 10, wherein the mouth of the blood permeable sac is closed when the apparatus is in the contracted configuration.

12. The apparatus of claim 11, wherein opposite sides of the support hoop close towards one another when the apparatus is contracted to its contracted configuration.

13. The apparatus of claim 1, wherein the support hoop comprises a radiopaque feature.

14. The apparatus of claim 13, wherein the radiopaque feature comprises a radiopaque wire wrapped around the spines of the support hoop.

15. The apparatus of claim 1, wherein the blood permeable sac has a length and a diameter that tapers along the length.

16. The apparatus of claim 1, wherein the support hoop is attached to a sheath slidably disposed on the elongated member.

17. The apparatus of claim 1 further comprising means for constraining longitudinal motion of the sheath with respect to the elongated member.

18. The apparatus of claim 1 further comprising an additional support hoop coupled to the distal region of the elongated member, having an articulation region comprising a gap interposed between curved spines.

19. A method of trapping emboli or thrombus during a medical procedure, the method comprising:

providing apparatus comprising an elongated member, a support hoop coupled to the elongated member, the support hoop having an articulation region comprising a gap, and a blood permeable sac affixed to the support hoop and bridging the gap;

positioning the apparatus in a contracted delivery state within a delivery sheath;

advancing the delivery sheath to a desired location within a patient's vessel;

withdrawing the delivery sheath; and expanding the apparatus to a deployed state, wherein the support hoop seals against the vessel wall.

20. The method of claim 19, wherein expanding the apparatus to a deployed state further comprises expanding the support hoop to engage the interior wall of the patient's vessel.

21. The method of claim 19 further comprising:

providing an interventional device comprising a guide wire lumen;

percutaneously and transluminally advancing the interventional device for performing a medical procedure along the elongated member to position within the patient's vessel at a location proximal of the apparatus;

performing the medical procedure, the apparatus catching emboli released when the medical procedure is performed;

retracting the apparatus into a collapsed configuration within the guide lumen of the interventional device; and removing the interventional device and apparatus from the patient's vessel.

22. The method of claim 21, wherein retracting the apparatus within the guide wire lumen comprises folding the support hoop at the articulation region.

23. The method of claim 19, wherein providing apparatus further comprises providing apparatus wherein the support hoop is coupled to a sheath slidably disposed on the elongated member, the method further comprising transmitting translational motion applied to the elongated member to the sheath without transmitting rotational motion applied to the elongated member.

* * * * *

UNITED STATES PATENT AND TRADEMARK OFFICE
CERTIFICATE OF CORRECTION

PATENT NO.   : 6,129,739
DATED        : October 10, 2000
INVENTOR(S)  : Farhad Khosravi It is certified that error appears in the above-identified patent and that said Letters Patent is hereby corrected as shown below:

Column 11,
Line 47, change "claim 1" to -- claim 16 --.

Signed and Sealed this

Twenty-first Day of August, 2001

*Attest:*

*Attesting Officer*

NICHOLAS P. GODICI
*Acting Director of the United States Patent and Trademark Office*